(12) United States Patent
Leo et al.

(10) Patent No.: US 6,461,595 B1
(45) Date of Patent: Oct. 8, 2002

(54) COSMETIC COMPOSITION IN THE POWDER FORM

(75) Inventors: Claudia Leo; Cristiane Rita Barros; Adriana Amaral Rodrigues, all of São Paulo-SP (BR)

(73) Assignee: Industria e Comercio de Cosmeticos Natura Ltda., Itapercerica Daserra (BR)

( * ) Notice: Subject to any disclaimer, the term of this patent is extended or adjusted under 35 U.S.C. 154(b) by 0 days.

(21) Appl. No.: 09/437,398

(22) Filed: Nov. 10, 1999

(30) Foreign Application Priority Data

Nov. 10, 1998 (BR) .............................................. 9804597

(51) Int. Cl.$^7$ ............................................... A61K 7/035
(52) U.S. Cl. ........................ 424/69; 424/401; 424/489
(58) Field of Search ............................ 424/63, 69, 401, 424/489

(56) References Cited

U.S. PATENT DOCUMENTS

| | | | |
|---|---|---|---|
| 3,611,583 A | 10/1971 | Anderson et al. ................ | 34/9 |
| 3,615,972 A | 10/1971 | Morehouse et al. .......... | 156/79 |
| 5,928,652 A | * 7/1999 | Bodelin-LeComte ....... | 424/400 |
| 5,939,079 A | * 8/1999 | Le Royer et al. ........... | 424/401 |
| 6,004,584 A | * 12/1999 | Peterson et al. ............ | 424/489 |

FOREIGN PATENT DOCUMENTS

| | | |
|---|---|---|
| EP | 0 056 219 A1 | 7/1982 |
| EP | 0 112 807 A2 | 7/1984 |
| EP | 0 310 472 A1 | 4/1989 |
| EP | 0 320 472 A1 | 6/1989 |
| EP | 0 379 409 A1 | 7/1990 |
| EP | 0 447 287 A1 | 9/1991 |
| EP | 0 462 709 A2 | 12/1991 |
| EP | 0 467 743 A1 | 1/1992 |
| EP | 0 486 080 A2 | 5/1992 |
| EP | 0 486 394 A1 | 5/1992 |
| EP | 0 502 769 A1 | 9/1992 |
| EP | 0 511 092 A1 | 10/1992 |
| EP | 0 530 085 A1 | 3/1993 |
| EP | 0 545 786 A1 | 6/1993 |
| EP | 0 566 442 A1 | 10/1993 |
| EP | 0 605 284 A1 | 7/1994 |
| EP | 0 651 991 A1 | 5/1995 |
| EP | 0 652 209 B1 | 5/1995 |
| EP | 0 692 242 A1 | 1/1996 |
| EP | 0 717 979 A2 | 6/1996 |
| EP | 0 704 205 A1 | 9/1996 |
| FR | 2 700 952 | 8/1994 |
| GB | 2 191 945 A | 12/1987 |
| GB | 2 275 190 A | 8/1994 |
| WO | WO 93/04660 | 3/1993 |

* cited by examiner

*Primary Examiner*—Jose' G. Dees
*Assistant Examiner*—Konata M. George
(74) *Attorney, Agent, or Firm*—Smith, Gambrell & Russell, LLP

(57) ABSTRACT

The present invention refers to a cosmetic composition in the powder form comprising a basic portion and a specific portion, wherein the basic portion comprises a first load of mois-touch lamellar particles of coated mica and a second load of dry-touch spherical particles with statistical size distribution of substantially up to 16 micra consisting of hollow silica microspheres, a binding compound and a carrier comprising a lamellar mineral load with particles below 10 micra, preferably micronized talcum powder.

30 Claims, No Drawings

COSMETIC COMPOSITION IN THE POWDER FORM

FIELD OF THE INVENTION

This invention refers to a cosmetic composition in the powder form for various applications, particularly those known as eye shadow, blush, face powder and compact makeup.

BACKGROUND OF THE INVENTION

Cosmetic compositions in the form of powder are well known and they are applicable as eye shadow, blush, face powder and compact makeup.

Most of said compositions present several disadvantages, such as being a complex composition and therefore expensive, demanding the use of manufacturing processes equally costly, they have a "sensorial" far from the desired one, and they prosent certain deficiencies after some time of use, such as cracking or general discontinuities.

Patent Application EP 310472 discloses a process for compacting such a cosmetic composition as well as an equipment for the execution of said process addressed to the manufacturing of compact powders, the major disadvantage of which is the need of specialized equipment, other than the usual commercially available standards, which increases the cost of the manufacturing process.

Patent Application EP 624361 discloses the manufacturing of cosmetic products in the form of powder which must include the addition of silica, silicon, or the spheres commercially known by the name of Expancel in order to be free from cracks, resulting in an expensive product and a complicated manufacturing process.

Patent Application EP 467743 discloses the manufacturing process of compact powders containing from 5 to 80% of thermoplastic products and which employs ultrasound for mixing its several components, also resulting in an expensive product and a complicated manufacturing process.

Patent Application EP 692242 describes the use of particles with a large granulometric specter, ranging from 1 to 250 microns, which are subject to deformation and as such, may present an undesirable sensorial variation depending on the different levels of pressure applied by the users at the time of using the product. To overcome this variable deformation disadvantage resulting from the differences of pressure applied by the users, the above mentioned application recommends that said particles be coated with lysine, which again raises the cost of the finished product, in addition of providing a sensorial effect which is not pleasant to all users.

Document EP 652209 describes the coating of various particles of cosmetic powders with a view of improving their compressibility.

Document EP 605284 describes a cosmetic composition which consists of a powder with a maximum density of 0.07 present in a range of 5 to 30% by weight. Such density of the powder substantially increases the difficulty of handling the product.

Another prior art document, namely EP 502769, discloses a cosmetic composition as a dispersion of solid particles which represent at least 50% by weight, or at least 75% by volume, in relation to the total load of particles, which present a spherical or spheroid shape with dimensions ranging from 0.5 to 50 microns. Said composition makes use of spherical or spheroid particles, a low content of lamellar particles, organic mineral material, or synthetic polymers, and pigments of smaller dimensions. Being a dispersion, the process for manufacturing same is costly and complicated, and by making use of small dimension pigments, it impairs their capacity of reflecting light, which would more satisfactorily correct small skin imperfections.

Document EP 651991 discloses a compound in the form of oil/water or water/oil emulsion for makeup containing mica, mica-titanium, white clay, zinc oxide and titanium, plane and expandable microspheres. As an emulsion, special equipment is required for its production which again increase the final costs.

Document EP 511092 describes the coating of microspheres in general, without any specific appeal.

Document EP 486394, on the other hand, describes the manufacturing of compact powders with the inclusion of hollow silica microspheres and solvents, resulting in a powder of difficult transportation which stains its own packaging and looks brittle.

Document GB 2 191 945 describes the use of microspheres in a noncompacted powder of synthetic material with an specific gravity of less than 0.1 g/cm$^3$, such as that which is commercialized under the name of Expancel, and which is disadvantageously limited for use in compositions of compacted form.

Document EP 717 979 discloses a compact powder composition that comprises an oily phase and a powdered phase, resulting in a product of the "powder-cream" type, the sensorial of which raises objections from many users, and which requires a step of freeze-drying, thus raising its final product cost.

Document EP 447 287 describes a cosmetic composition limited to compositions of the compact type, comprising porous microspheres of thermoplastic material. This application describes as being advantageous the association of such microspheres, known as Expancel, to micronized talcum powder and hexagonal boron nitride. The use of said porous microspheres necessarily associated with the hexagonal boron nitride does not warrant a sensorial accepted by most of the users, in addition to raising the cost of the product.

Document EP 462 709 describes a cosmetic composition comprising, among several ingredients, particulated nylon smaller than 20 microns. Said composition is not satisfactory concerning sensorial, and also presents a non competitive cost.

Document EP 530 085 discloses a cosmetic composition in the form of a stable dispersion in an aqueous phase, containing two types of hydrosoluble acrylic polymers. As previously discussed, being a dispersion, its final cost is elevated.

Likewise, document EP 545786 discloses a composition in the form of a dispersion in an adequate ligand, in the presence of perfluoralkyl, which is formulated in the form of a water/oil or oil/water emulsion with the oil phase representing up to 50% of the total weight of the composition.

It should be noted that a great portion of the already known solutions make use of hollow expansible microspheres with a view to obtaining cosmetic powders, which is a product of extremely high cost and of difficult availability in the market.

The obtaining of these and other similar microspheres, and the application thereof into cosmetic compositions which generically are either too expensive or fail to provide the desired sensorial effect, is described in several other patent documents, which are hereby incorporated by reference, such as U.S. Pat. No. 3,615,972, EP 056 219, U.S.

Pat. No. 3,611,583, EP 112 807, EP 320 472, EP 379 409, EP 486 080, WO 93/04660, EP 566 442, FR 9 300 990 and EP 704 205.

OBJECTIVES OF THE INVENTION

It is, therefore, an objective of the present invention to provide a cosmetic composition in the form of a powder that overcomes all the disadvantages of the prior art, by presenting an ultrafine texture without having the consistence of a cream, since it does not contain a high concentration of oily ingredients.

It is further desired that the adherence of said composition to the skin be not provided solely by the characteristics of the oily phase, but also by the lamellar shape of some of the components of its formulation.

It is also an objective of the invention to provide a cosmetic powder composition which allows its easy manipulation without making use of expensive processes and materials, and which is capable of minimizing small skin defects without resulting in the aspect of an artificial skin. Further to that, its texture must facilitate the application of the product without interfering in the grinding and compacting process, particularly due to the presence of microspheres derived from organic material.

Additionally, it is also required that an adequate selection of the nature of the ingredients as well as the percentage thereof is effected so that the composition may result in an improved synergy, integrating the ingredients in such way as to advantageously include cosmetic materials such as the microspheres of marine collagen that maintain the natural moisturizing of the skin without any vestige of non-homogeneity or discontinuities in general.

Another equally important objective of the invention is providing a cosmetic powder composition that allows the production of a basic portion common for eye shadow, blush, face powder and compact makeup, subsequently associated to specific portions that will define each of the above mentioned compositions, thus facilitating the industrial logistics.

SUMMARY OF THE INVENTION

The present invention refers to a cosmetic powder composition comprising a basic portion and a specific portion, wherein the basic portion comprises a first load of lamellar moist-touch particles of coated mica, and a second load of dry-touch spherical particles with a statistical size distribution of substantially up to 16 microns, comprising silica microspheres, a ligand and a carrier comprising a mineral lamellar load with particles smaller than 10 microns, preferably micronized talcum powder.

DETAILED DESCRIPTION OF THE INVENTION

As far as the advantageous sensorial effect is concerned, the results of the invention begin to be achieved with the preparation of the basic portion with excellent properties of spreadability and softness, as well as its integrity, being free of cracks and general discontinuities, even after a long period of use.

According to the invention, the dry-touch and moist-touch particles are selected from particles that can be compacted, particles that cannot be compacted, and mixtures thereof. The particles that cannot be compacted may be of the spherical mineral type, substantially hollow silica microspheres with a phenomenal surface ranging from 50 to 120 $m^2/g$, preferably of about 70 $m^2/g$, adapted for providing specular light diffusion.

In a preferred form of the composition of the invention, mica is coated with an aminoacid, preferably lauryl lysine, and the ligand comprises branched synthetic esters selected from the group of pentaerythritol tetraester, stearoyl isocethyl stearate, a water repellent and skin conditioner compound selected from synthetic ethers from the group of polyperfluoroisopropyllic ether.

Preferably the composition according to the invention presents a content, in weight percent, of about 1.0 to 40.0%, preferably of 1 to 30% of coated mica; 0.1 to 20%, preferably 0.3 to 10% of silica microspheres;, 0.1 to 8%, preferably 0.1 to 6% of pentaerythritol tetraester; 0.05 to 9.5%, preferably of 0.1 to 7% of isocethyl stearoyl stearate; 0.01 to 5%, preferably 0.05 to 3.0% of synthetic ethers from the group of polyperfluoroisopropyllic ether; and 40 to 100%, preferably 50 to 97% of the carrier, being micronized talcum powder.

As to the specific portion comprised in the composition here described, it preferably contains 2.00 to 30.0%, of optionally coated pigments; 0.05 to 2%, preferably of 0.1 to 1.2%, of preservatives and 0.01 to 0.5%, preferably of 0.03 to 0.3% of antioxidant.

In another preferred embodiment of the invention, the specific portion may also include from 0.01 to 0.5% of fragrances and sufficient quantity of a solvent, as well as 0 to 5%, preferably 0 to 3%, of a cosmetic treatment compound such as the marine collagen microspheres (Atelocollagen Sodium Condroitin sulfate).

Said basic portion may be associated with compounds that will confer variable cosmetic attributes depending on the desired final product that may be blush, eye shadow and face powder or compact makeup.

When the composition according to the invention is formulated to be used as an eye shadow, for instance, it preferably comprises a specific portion comprising a compound for facilitating the adherence to the skin, preferably boron nitride, in a range of 0 to 10%, preferably of 0 to 5%, by weight.

It may also have a specific portion which further includes, a polyurethane compound, silica and their mixtures, such as hexyldexyldiisocianate/trimetilol hexyllactone crosspolimer and silica in a range from 1 to 4%, preferably about 3.0%; from 18 to 27%, preferably about 24% of pigments; from 2 to 4%, preferably about 3% of a binding compound, such as the isocetylstearoyl stearate and from 1 to 4%, preferably around 2.5% of pentaerithritol tetraester; from 0.03% to 0.9%, preferably from 0.05% to 0.7% of preservatives and antioxidants, from 0.01 to 2.0%, preferably about 0.2%, of synthetic wax, the remaining being a micronized talcum powder compound.

When the composition of the invention is prepared to be a blush, it preferably has a specific portion further comprising a polyurethane compound and silica, as well as mixtures thereof, such as from 1.0 to 3.0%, preferably about 2.5% of hexyldexyldiisocianate/trimetilol hexyllactone crosspolimer and silica; from 8 to 15%, preferably about 9.0% of pigments; from 2 to 4%, preferably about 3% of a binding compound such as isocetyl stearoyl stearate and from 1 to 5%, preferably about 3.0% of pentaerithritol tetraester; from 0.03% to 0.9%, preferably about 0.7% of preservatives and antioxidants, from 0.01 to 1.2%, preferably about 0.5%, synthetic wax, the remaining being composed of about 0.02 to 0.07% of solvents and micronized talcum powder.

For a formulation for a face powder, the composition preferably has pigments preferably coated with fluoralcohol phosphate in a range from 4 to 12%; cosmetic treatment compound in a range from 0.2 to 0.7%, preferably about 0.4% such as sea origin collagen microspheres (Sodium Athelocollagen Condroitinsulphate); binding compound, such as the isocetylstearoyl stearate in a range from 0.2 to 6%, preservatives and antioxidants in a range from 0.03 to 1.5%, preferably from 0.05% to 0.9%, the remaining consisting of solvents in a range of about 0.02% to 0.2% and micronized talcum powder.

As compact powder, a preferred composition comprises in its specific portion a polyurethane compound and silica, and their mixtures, such as the hexildecildiisocianate/trimethylol hexillactone crosspolimer and silica, in a range from 2.5 to 8.0, preferably about 5.0%; a binding compound selected from pentaeritHritol tetraester in a range from 2 to 5%, preferably about 3.5% and synthetic waxes and their mixtures in a range from 0.1 to 1.0%, preferably about 0.4%.

The cosmetic powder composition according to the invention, has soft, tender, velvet-like, powder and non-fatty texture which makes the application of the product easier.

Another advantage of the invention is its higher adhesion to the skin, colour faithfulness, its capacity to minimize small imperfections of the skin, maintaining the natural aspect of the make-up, excellent fluidity and water resistance, which increases the time of permanence of said composition on the skin, thus minimizing the need to make retouches.

Another advantage of the invention is the maintenance of the natural skin moisture due to the possibility of including components such as sea origin collagen microspheres.

Another advantage of the invention is its notable comfort at the moment of application, in addition of containing no toxic or irritating compounds.

Moreover, one further advantage of the present invention comes from the simplified grinding process to obtain same, which is possible because of the selection of spherical materials, such as hollow and non-hollow spheres associated to lamellar particles, which make the use of complicated manufacturing means, such as the micronization process, dispensable.

To provide a better understanding of the present invention, the applicant presents below some illustrative examples which refer merely to some embodiments of the present invention, and should not be taken in any way to limit the scope thereof which is defined in the following claims. The components or ingredients concentrations showed in the examples are expressed as a weight percentage based on the total weight of the composition, unless specifically stated in a different way.

EXAMPLE I

According to a first preferred embodiment of the invention intended for the production of shadow for the area of the eyes, a cosmetic composition was prepared comprising:

Basic Portion
moist-touch lamellar particles (coated mica: 30%)
dry-touch spherical particles (silica microspheres: 1.5%)
binding compound (association of esters and synthetic wax: 8%)
carrier (micronized talcum powder: about 40%)
Specific Portion
moist-touch spherical particles (polyurethane and silica: 8%)
boron nitrate (a compound that facilitates the adhesion on the skin: 2.5%)
water repellent compound (polyperfluoroisopropylic ether: 0.1%)
preservatives and antioxidants: about 0.6%
pigments: about 15% and varying according to the desired colour of the final product

EXAMPLE II

In another embodiment of the invention intended to be used as a blush, a cosmetic composition was prepared comprising:
Basic Portion
moist-touch lamellar particles (coated mica: 11%)
dry-touch spherical particles (silica microspheres: 2.0%)
binding compound (association of esters and synthetic wax: 5%)
carrier (micronized talcum powder: about 55%)
Specific Portion
moist-touch spherical particles (polyurethane and silica: 3%)
water repellent compound (polyperfluoroisopropylic ether: 0.1%)
preservatives and antioxidants: about 0.6%
fragrance and solvent around 0.1%
pigments: about 24% and varying according to the desired colour of the final product

EXAMPLE III

In a third form to perform the invention specifically intended for face or face powder, a cosmetic composition was prepared comprising:
Basic Portion
moist-touch lamellar particles (coated mica: 4%)
dry-touch spherical particles (silica microspheres: 0.1%)
binding compound (association of esters: 1%)
carrier (micronized talcum powder: about 84%)
Specific Portion
cosmetic treatment compound (microspheres of sea collagen: 0.65%)
water repellent compound (polyperfluoroisopropylic ether: 0.1%)
preservatives and antioxidants: about 0.6%
fragrance and solvent, around 0.2%
pigments: about 10% and varying according to the desired colour of the final product

EXAMPLE IV

In another embodiment of the invention, a composition for compact powder was prepared having the following characteristics:
Basic Portion
moist-touch lamellar particles (coated mica: 8%)
dry-touch spherical particles (silica microspheres: 4.5%)
binding compound (association of esters and synthetic wax: 10%)
carrier (micronized talcum powder: about 63%)
Specific Portion
cosmetic treatment compound (microspheres of sea collagen: 0.65%)
water repellent compound (polyperfluoroisopropylic ether: 2.5%)

preservatives and antioxidants: about 0.6% fragrance and solvent, around 0.2% pigments: about 10% and varying according to the desired colour of the final product

EXAMPLE V

The Chart below shows other formulations for compositions to be used as eye shadow, blush, compact powder and face powder:

| Compound | Eye Shadow | Blush | Compact Powder | Face Powder |
|---|---|---|---|---|
| Talcum Powder (carrier) | qs 100% | qs 100% | qs 100% | qs 100% |
| Coated mica (wet touch) | about 30.00% | about 15.00% | about 15.00% | about 10.00% |
| Silica Beads (dry touch) | about 2.50% | about 3.00% | about 6.00% | about 1.00% |
| Polyurethane and Silica (wet touch) | about 4.00% | about 4.00% | about 6.00% | — |
| Synthetic Wax (binder) | about 0.07% | about 1.00% | about 1.00% | — |
| Boron Nitrate (adhesion) | about 3.00% | — | — | — |
| Isocetyl Stearoyl Stearate (binder) | about 5.00% | about 5.00% | about 6.00% | about 1.00% |
| Pentaerythritol Tetraester (binder) | about 3.75% | about 4.00% | about 5.00% | about 1.00% |
| Polyperfluoroisopropylic Ether (water repellant) | about 0.30% | about 0.30% | about 2.00% | about 0.20% |
| Microspheres of sea collagen (cosmetic treatment): | — | — | about 0.65% | about 0.65% |
| Preservatives | 0.50% | 0.50% | 0.50% | 0.50% |
| Antioxidants | 0.05% | 0.05% | 0.05% | 0.05% |
| Alcohol | — | 0.05% | 0.10% | 0.05% |
| Fragrance | — | 0.03% | 0.05% | 0.03% |
| Pigments | qs | qs | qs | qs |
| Presentation of the product in the market | Compact | Compact | Compact | loose |

What is claimed is:

1. A cosmetic composition in the powder form, comprising:
   a basic portion that comprises
      a load of moist-touch lamellar particles of coated mica coated with lauryl lysine,
      a load of dry-touch spherical particles with statistical size distribution of up to 16 microns consisting of silica microspheres,
      a binding compound including branched synthetic esters selected from the group consisting of pentaerythritol tetraester, stearoyl isocetylstearate, and mixtures thereof, and
      a carrier comprising a lamellar mineral load with particles smaller than 10 microns;
   a specific portion; and
   a polyperfluoroisopropylic ether.

2. The composition according to claim 1, wherein the carrier is micronized talcum powder.

3. The composition according to claim 1, wherein the moist-touch particles and dry-touch particles are selected from
   particles that can be compacted,
   particles that cannot be compacted, and
   mixtures thereof.

4. The composition according to claim 3, wherein the particles that cannot be compacted consist of spherical mineral particles, substantially hollow silica microspheres with phenomenal surface area between 50 and 120 $m^2/g$, adapted to provide specular light diffusion.

5. The composition according to claim 4, wherein the particles that cannot be compacted have a phenomenal surface area of about 70 $m^2/g$.

6. The composition according to claim 1, wherein the moist-touch lamellar particles of coated mica, are coated with at least one amino acid;
   the binding compounding includes branched synthetic esters;
   and the composition further comprises a water repellent compound and a skin conditioner.

7. A cosmetic composition in the powder form, comprising:
   a basic portion that comprises
      1.0–40 wt. % of a load of moist-touch lamellar particles of coated mica,
      0.1–20 wt. % of a load of dry-touch spherical particles with statistical size distribution of up to 16 microns consisting of silica microspheres,
      a binding compound, and
      a carrier comprising a lamellar mineral load with particles smaller than 10 microns;
      0.1–8.0 wt. % pentaerythritol tetraester;
      0.05–9.5 wt. % stearoyl isocetylstearate;
      0.01–5.0 wt. % of at least one polyperfluoroisopropylic ether;
      greater than 40 wt. % of a carrier of micronized talcum powder; and
   a specific portion.

8. The composition according to claim 1, comprising, 1.0–30 wt. % coated mica;
   0.3–10 wt. % silica microspheres;
   0.1–6.0 wt. % pentaerythritol tetraester;
   0.1–7.0 wt. % stearoyl isocetylstearate;
   0.05–3.0 wt. % of at least one polyperfluoroisopropylic ether; and
   50.0–97.0 wt. % of a carrier of micronized talcum powder.

9. The composition according to claim 1, wherein the specific portion comprises:
   0.1 to 1.2 wt. % of at least one coated pigment;
   0.05 to 2 wt. % of at least one preservative; and
   0.01 to 0.5 wt. % of at least one antioxidant.

10. The composition according to claim 9, wherein the specific portion comprises:
    0.1 to 1.2 wt. % of at least one preservative; and
    0.03 to 0.3 wt. % of at least one antioxidant.

11. The composition according to claim 1, being formulated for a shadow for the area of the eyes, wherein the specific portion contains a compound that facilitates the adhesion of the skin.

12. The composition according to claim 11, wherein the specific portion contains boron nitrate that facilitates the adhesion of the skin.

13. The composition according to claim 12, wherein the specific portion contains up to 10.0 wt. % of a compound that facilitates the adhesion of the skin.

14. The composition according to claim 13, wherein the specific portion contains up to 5.0 wt. % of boron nitrate that facilitates the adhesion of the skin.

15. The composition according to claim 11, being formulated for a shadow for the area of the eyes, wherein the specific portion further contains
   a polyurethane compound or silica, and mixtures thereof.

16. A cosmetic composition in the powder form and being formulated for a shadow for the area of the eyes, comprising:

a basic portion that comprises
  a load of moist-touch lamellar particles of coated mica,
  a load of dry-touch spherical particles with statistical size distribution of up to 16 microns consisting of silica microspheres,
  a binding compound, and
  a carrier comprising a lamellar mineral load with particles smaller than 10 microns; and
a specific portion contains containing
  a compound that facilitates the adhesion of the skin,
  a polyurethane compound or silica, and mixtures thereof; at least one pigment in a range from 18 to 27 wt. %,
  the binding compound isocetylstearoyl stearate in a range from 2 to 4 wt. % and/or pentaerythritol tetraester in a range from 1 to 4 wt. %,
  at least one preservative and at least one antioxidant in a combined amount range of from 0.03 to 0.9 wt. %,
  at least one synthetic wax in a range of from 0.01 to 2.0 wt. %, and
  micronized talcum powder; wherein
the polyurethane is hexyldecyldiisocyanate/trimethylol hexyllactone crosspolymer and silica is present in a range from 1 to 4.0 wt. %.

17. The composition according to claim 16, being formulated for a shadow for the area of the eyes, wherein
the silica is present in a range from 1 to 3.0 wt. %,
and further comprises
  one or more pigments in a range amount totaling about 24%;
  the binding compound isocetylstearoyl stearate in an amount of about 3 wt. % and/or pentaerythritol tetraester in an amount of about 2.5 wt. %;
  at least one preservative and at least one antioxidant in a combined amount range of from 0.05 to 0.7 wt. %,
  at least one synthetic wax in an amount of about 0.2 wt. %,
  the remaining consisting of micronized talcum powder.

18. A cosmetic composition in the powder form, comprising:
a basic portion that comprises
  a load of moist-touch lamellar particles of coated mica,
  a load of dry-touch spherical particles with statistical size distribution of up to 16 microns consisting of silica microspheres,
  a binding compound, and
  a carrier comprising a lamellar mineral load with particles smaller than 10 microns; and a specific portion, wherein the specific portion further includes a solvent and at least one fragrance in a range amount from 0.01 to 0.5 wt %.

19. The composition according to claim 18, being formulated as a blush, wherein the specific portion further contains a polyurethane compound or silica, and mixtures thereof.

20. The composition according to claim 18, being formulated as a blush, wherein
the polyurethane is hexyldecyldiisocyanate/trimethylol hexyllactone crosspolymer and
silica is present in a range from 1.0 to 3.0 wt. %,
and further comprises
  at least one pigment in a range from 8 to 15 wt. %,
  the binding compound isocetylstearoyl stearate in a range from 2 to 4 wt. % and/or pentaerythritol tetraester in a range from 1 to 5 wt. %,
  at least one preservative and at least one antioxidant in a combined amount range of from 0.03 to 0.9 wt. %,
  at least one synthetic wax in a range of from 0.1 to 1.2 wt. %,
  at least one solvent and
  micronized talcum powder.

21. The composition according to claim 20, being formulated as a blush, wherein
the silica is present in an amount of about 2.5 wt. %,
and further comprises
  one or more pigments in a range amount totaling about 9.0 wt. %;
  the binding compound isocetylstearoyl stearate in an amount of about 3 wt. % and/or pentaerythritol tetraester in an amount of about 3.0 wt. %;
  at least one preservative and at least one antioxidant in a combined amount of about 0.7 wt. %,
  at least one synthetic wax in an amount of about 0.5 wt. %,
  the remaining consisting one or more solvents and micronized talcum powder.

22. The composition according to claim 21, wherein the specific portion further includes a cosmetic treatment agent in a range from 0 to 5 wt. %.

23. The composition according to claim 21, wherein the specific portion further includes a cosmetic treatment agent in a range from 0 to3 wt. %.

24. A cosmetic composition in the powder form, comprising:
a basic portion that comprises
  a load of moist-touch lamellar particles of coated mica,
  a load of dry-touch spherical particles with statistical size distribution of up to 16 microns consisting of silica microspheres,
  a binding compound, and
  a carrier comprising a lamellar mineral load with particles smaller than 10 microns; and a specific portion, wherein the specific portion further includes a cosmetic treatment agent that comprises sea collagen microspheres.

25. The composition according to claim 24, wherein the sea collagen microspheres are sodium atelocollagen condroitinsulphate.

26. A cosmetic composition in the powder form and being formulated as a face powder comprising,
a basic portion that comprises
  a load of moist-touch lamellar particles of coated mica,
  a load of dry-touch spherical particles with statistical size distribution of up to 16 microns consisting of silica microspheres,
  a binding compound, and
  a carrier comprising a lamellar mineral load with particles smaller than 10 microns;
  a specific portion,
  one or more pigments coated with phosphate fluoroalcohol in an amount ranging from 4 to 12 wt. %,
  a cosmetic treatment agent in a range from 0.2 to 0.7 wt. %,
  a binding compound of isocetylstearoyl stearate in a range from 0.2 to 6 wt. %,
  at least one preservative and at least one antioxidant in a combined amount range of from 0.03 to 1.5 wt. %,
  at least one solvent in a range of from 0.02 to 0.2 wt. % and
  micronized talcum powder.

27. The composition according to claim 26, being formulated as a face powder and comprising
  a cosmetic treatment agent of sea origin collagen microspheres in an amount of 0.4 wt. % and further comprises
    at least one preservative and at least one antioxidant in a combined amount range of from 0.05 to 0.9 wt. %.

28. The composition according to claim 27, being formulated as a compact face powder, wherein the specific portion further contains
    a polyurethane compound or silica, and mixtures thereof.

29. The composition according to claim 28, being formulated as a compact face powder, wherein
    the polyurethane is hexyldecyldiisocyanate/trimethylol hexyllactone crosspolymer and
    the silica is present in a range of 2.5 to 8.0 wt. %,
    and further comprises
        binding compound pentaerythritol tetraester in a range of 2 to 5 wt. %;
        at least one synthetic wax in a range of 0.1 to 1.0 wt. %.

30. The composition according to claim 28, being formulated as a compact face powder, wherein
    the silica is present in an amount of about 5.0 wt. %,
    and further comprises binding compound pentaerythritol tetraester in an amount of about 3.5 wt. % and at least one synthetic wax in an amount of about 0.4 wt. %.

* * * * *